United States Patent [19]

Zelno

[11] Patent Number: 5,591,117
[45] Date of Patent: Jan. 7, 1997

[54] METHOD AND AN APPARATUS FOR THE DISPOSAL OF MATERIAL CONTAINING INFECTIVE MICROORGANISMS

[76] Inventor: Heinz Zelno, Bgm.-Aurnhammer-Str. 13, 86199 Augsburg, Germany

[21] Appl. No.: 243,453

[22] Filed: May 16, 1994

[51] Int. Cl.⁶ .................................................. A62D 3/00
[52] U.S. Cl. .................... 588/258; 134/102.1; 210/760; 422/186.07; 405/128; 588/244
[58] Field of Search .................................... 588/249, 258; 405/128; 422/28–33, 186.07; 134/102.1, 102.2; 210/760

[56] References Cited

U.S. PATENT DOCUMENTS

| | | | |
|---|---|---|---|
| 5,207,237 | 5/1993 | Langford | 422/28 X |
| 5,370,801 | 12/1994 | Soresen et al. | 210/942 |
| 5,377,917 | 1/1995 | Wiljan et al. | 241/14 |

*Primary Examiner*—Dennis L. Taylor
*Attorney, Agent, or Firm*—Edwin D. Schindler

[57] ABSTRACT

The disposal of material containing infective microorganisms such as bacteria, fungi and viruses and more especially for the disposal of waste from medical facilities such as clinics and medical practices or the like may be performed in a simple and economic reliable fashion to provide satisfactory area coverage if the substrate is introduced into a container (1) able to be charged with ozone and exposed therein to the action of the ozone until the microorganisms are killed, after this the ozone is discharged from the container (1) and is converted to a lower valence level and the container (1) is then evacuated.

8 Claims, 1 Drawing Sheet

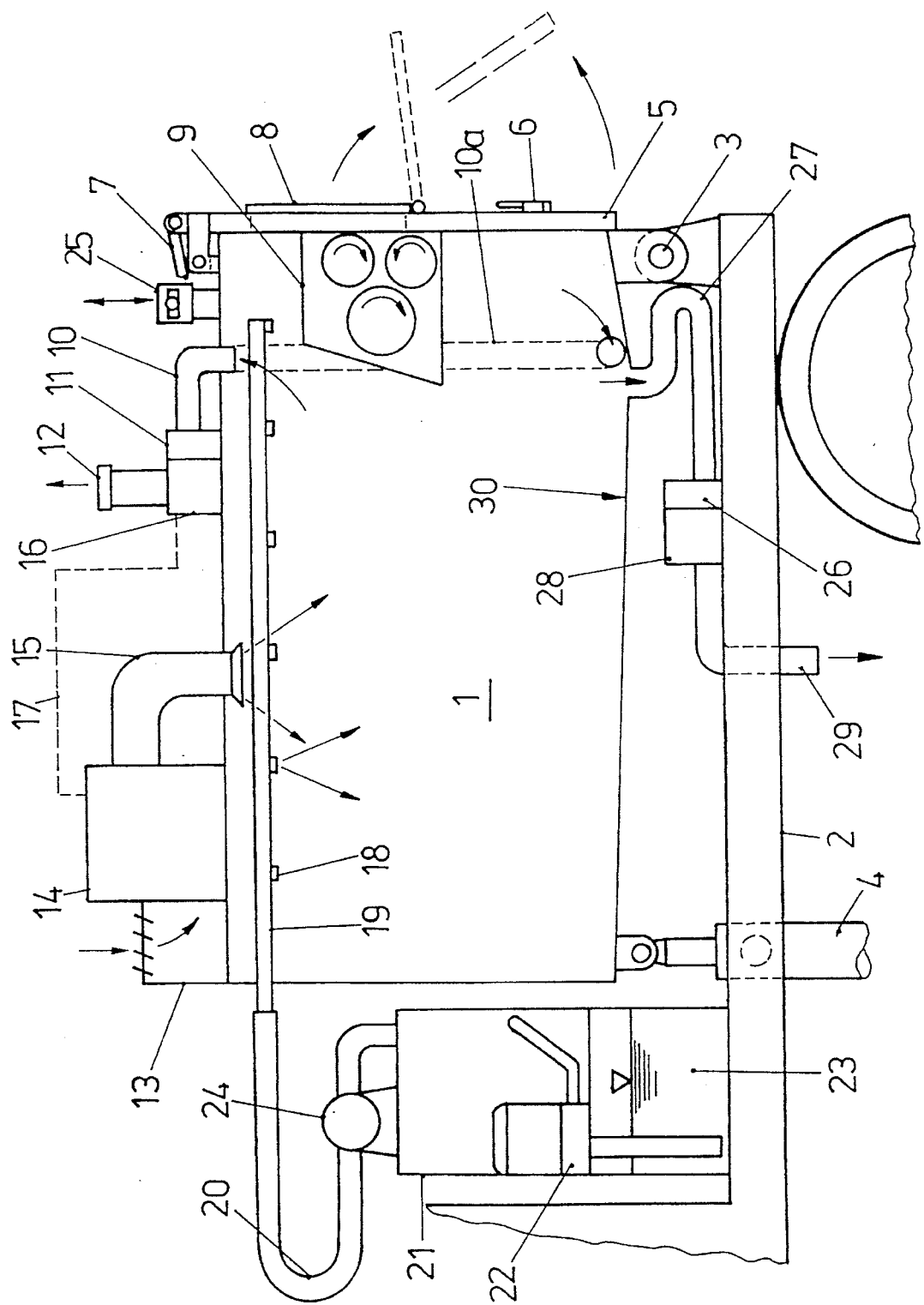

METHOD AND AN APPARATUS FOR THE DISPOSAL OF MATERIAL CONTAINING INFECTIVE MICROORGANISMS

The invention relates to a method for the disposal of material containing infective microorganisms such as bacteria, fungi and viruses and more especially for the disposal of waste from medical facilities such as clinics and medical practices or the like and to an apparatus suitable for the performance of the method.

Material contaminated with infective microorganisms of this type has so far often simply been dumped without any preparation or, if there are incineration facilities, burnt. While such incineration doses kill off the microorganisms, the material as such however frequently consists of synthetic resins and the like, whose incineration is not without environmental problems and the combusted material from such incineration has to be handled as special or hazardous waste. A further disadvantage arises because of the substantial amount of energy required for the incineration. A particularly serious problem is that the incineration is only performed at a limited number of points and does not provide effective area coverage so that high transport and storage costs have to be absorbed if incineration is not to be abandoned as being insupportably expensive.

Taking this as a starting point, one object of the present invention is to create a method and an apparatus of the type initially mentioned suitable for the disposal of waste contaminated with microorganisms which is economic even when providing full area coverage, is highly compatible with efforts to protect the environment.

In accordance with the invention this aim is to be attained for the method asspect by the introduction of the substrate into a container able to be charged with ozone and exposed therein to the action of the ozone until the microorganisms are killed, that after this the ozone is discharged from the container and is converted to the lower oxygen valence and the container is then evacuated.

The apparatus in accordance with the invention for the performance of this method comprises a container adapted to be closed provided with an inlet opening and an outlet opening, comprising at least one ozone duct opening into the internal space of the container and extending from an associated ozone producing device, and whose internal space is connected at least one exhaust duct, which runs to an aspiration device, with which a de-ozonizing device is connected.

The ozone to which the contaminated materials are subjected, is responsible for a reliable killing of all infective microorganisms within a comparatively short time without other materials being attacked. The disinfected material resulting after the disinfection may consequently simply be added to household refuse or disposed of as such. There is the advantage that no hazardous waste is produced. A still further advantage of the measures contemplated by the invention is that ozone may simply be obtained from sources of oxygen such as water or air by conversion to its higher valence state and disposed of again simply by a conversion to the lower valence condition. There is the advantage that no aggressive wastes are likely. In fact the medium produced by de-ozonizing may be readily discharged into the environment. The apparatus required for the performance of the method in accordance with the invention is comparatively simple and economic and offers the further advantage of being able to be manufactured in a portable version so that at comparatively low expense good coverage of a wide area can be ensured.

Further advantageous forms and convenient further developments of the invention are recited in the dependent claims. Thus it is possible, as an advantage of the invention, for the substrate to be comminuted on being introduced into the container. Such comminution is not only responsible for good utilization of the space available of the volume of the container but also simultaneously improves the possibilities for the ozone to react, something which is advantageous as regards the ozone treatment times required and furthermore the reliability of the disinfection.

In accordance with a further possible measure for the ozone treatment ozonized air is employed. There is the advantage that air is available everywhere at no cost and may be ozonized simply by altering the valence of the oxygen present (from $O_2$ to $O_3$). The ozonized air represents a gaseous medium, which has the advantage of being able to penetrate into cavities, something which guarantees a reliable action on the entire contents of the container.

As an additional or alternative feature ozonized water can be utilized for the ozone treatment. Here as well ozonization is performed by altering the valence of the oxygen present in the air ($H_2O$ to $H_2O_3$). There is then the advantage of being able to spray the liquid ozonized in this manner onto the contents of the container so that there is a satisfactory wetting of the entire contents of the container. Furthermore it is in this case possible to relatively quickly achieve the desired zone concentration of around 30 to 40%.

It is convenient to move the substrate in the container in order to attain thorough mixing in and pervasion of the ozone. This is something which may be achieved in a simple fashion by tipping the container up and down, that is to say with the aid of a device, which may be employed for emptying the container as well. Therefore no additional means are required.

A further expedient feature of the invention may be that the container is at least partly evacuated prior to subjection to the action of the ozone. Accordingly it is then feasible to ensure the ozone concentrations relatively quickly by a satisfactory distribution throughout the volume of the container contents.

As a further advantageous feature the container may be mounted on a vehicle. This leads to the advantage of high mobility and good economic performance.

It is convenient for the floor of the container to be in the form of a sump whose lowest point has a suction duct extending from it, which leads to a suction pump, which for its part follows a liquid deozonizing catalyst from which an outlet port is directed. These features serve to ensure a reliable removal of the ozonized liquid from the container and the return thereof to the original valence so that the medium produced in this case may be discharged into the surroundings, for example into a sewage system.

In accordance with a further development of the invention it would be feasible for an evacuating duct to extend from the container which leads to an evacuating pump, which is followed by a gas de-ozonizing catalyst, from which an outlet port leads. These features represent a simple way of both evacuating the container prior to ozone treatment simply by pumping the container free of air, and also of removal of ozonized gas, for example of ozonized air and rendering it inactive.

Further convenient developments and advantageous designs of the invention are recited in the remaining dependent claims and will be seen from the following description of an example thereof.

In what follows one embodiment of the invention will be described in more detail, whose single figure shows a diagrammatic view of a disposal vehicle in accordance with the invention.

The disposal vehicle illustrated in the drawing possesses a closable container 1 which is manufactured of oxidation-resistant material such as stainless steel in the form of V4A steel or plastic or the like, is gas- and liquid-tight and which in this case is mounted on a chassis 2 of a truck. It would however naturally be feasible for such container to be stationarily arranged. The container 1 is able to be tipped at its rear end using a pivot bearing 3 mounting it on the chassis 2 and may be raised the lowered by means of a lifting device acting on its front end. The rear end side of the container is designed to constitute a removal opening, which is able to be shut by means of a door 5 pivoted at its top edge. Such door is able to be locked in the operational position by locking means 6 so that there is a gas- and liquid-tight unit. For emptying the container 1 it is possible for the door 6 to be pivoted backward as indicated by a directional arrow and an outwardly pivoted position indicated in full lines. This may take place after releasing the locking means and upwardly tipping the container 1 automatically or, as in the present case, may be aided by a pivoting unit 7.

Waste contaminated with infective microorganisms from medical practices, clinics and the like is placed in the container 1. For this purpose adjacent to the door 5 there is a receiving opening, which for its part is able to be shut by a door 8. Adjacent to the receiving opening there is a comminuting device 9 for the comminution of the material thrown into the container. This comminution device may, as shown in working embodiment, be attached to the door 5, but it would be possible t mount the comminuting device 9 on the door 8 for the receiving opening and which on opening the receiving opening with the door associated with it would be tipped out of the container 1. In the illustrated working embodiment of the invention in its open setting, as shown in broken lines, the door 8 constitutes a delivery table associated with the comminuting device 9. In order to distribute the material placed in the container 1 over the full volume of the container it is simply possible to perform several lifting and lowering movements using the lifting unit 4. However it would readily be feasible to provide a suitable distributing device inside the internal space of the container.

In order to render the material placed in the container 1 free of microorganisms it is subjected to the action of ozone until the microorganisms are killed off. Using a concentration of ozone equal to 30 to 40% of the total volume of the container after a period of action of 30 to 40 minutes all microorganisms will be reliably killed. For this purpose the container 1 filled with the contaminated material is subjected to the action of one or more ozonized media. In this respect it is a question of media at least containing oxygen which has be changed in a higher valence state. Thus air can be ozonized by converting the oxygen therein from $O_2$ to $O_3$. Water can be ozonized by converting its composition from $H_2O$ to $H_2O_3$.

Since ozone is heavier than air the air may be displaced from the container 1 by an ozonized medium introduced into the container 1. To permit outflow of the displaced medium from the container 1 the latter may simply be provided with an upper outflow opening. During such outflow from such opening however a careful watch is required in order to prevent escape of ozone and furthermore such displacement operation is only suitable for comparatively low ozone concentrations. In the illustrated working embodiment of the invention the air present in the container 1 is consequently drawn off from the container 1 prior to charging the container wilt ozone. For this purpose an evacuating line 10 extending from the container 1 is provided, which leads to an evacuating pump. The air drawn by the same from the container 1 can be discharged into the surroundings via a discharge port 12. In order to render possible such evacuation but then afterwards to hinder escape of ozone the container 1 is, as described above, provided with means for sealing the same in a gas- and liquid-right fashion.

After completion of the evacuation of the container the same is charged with ozone. For this purpose it is possible to utilize a pressure container with an ozonized medium or pure ozone and also mounted on the chassis 2 and which is connected with the container 1 for charging it with ozone. Furthermore it would be feasible to employ an external, separate ozone source.

In the illustrated working embodiment of the invention the production of ozone is performed on site by ozonization of air taken from the surroundings and of water carried in a tank or taken from the public water supply. The air is taken from the surroundings by means of an aspirator 13 and supplied to an ozone generator 14 designed for the ozonization of gases such as air, from which generator there leads an injection nozzle 15 provided with a diffusor. If the first ozone charge therein is insufficient to achieve the desired ozone concentration in the container, it is possible for the evacuation operation to be repeated as frequently as necessary until the required concentration is attained. However it would be feasible to charge the container 1 with ozone and simultaneously to draw it off. In order in cases of this type to prevent escape of ozone the evacuating pump 11 is followed by a gas de-ozonizing catalyst 16. In order to economize in the use of ozone the evacuating pump 11 may have its outlet connected by means of a short circuit line 17 with the inlet of the ozone generator 14 so that the latter merely has to perform the further ozonization still required and only a short charging time is necessary before the desired concentration is attained.

Instead of air as the source of ozone it would naturally be feasible to utilize pure oxygen from a gas cylinder. Additionally or as an alternative to ozonized gas it would be feasible, as described above, to employ ozonized liquids and preferably ozonized water. For this purpose in the upper part of the container a nozzle beam 19 is installed having spraying nozzles 18, such beam being connected via a supply line 20 with an ozone generator 21 for ozonizing liquids such as water. The ozone generator 21 is supplied from a pump 22, which via its suction port is able to take water from a tank 23. The tank 23 and furthermore the ozone generator 21 and the pump 22 arranged between them are fixed on the chassis 2. The supply line 20 running to the portable container 1 is accordingly in the form of a hose duct provided with a length take-up loop. The means on the air side for the evacuation and charging of the container 1 are in the illustrated working embodiment mounted on the container 1 itself so that in this case fixed piping may be employed.

The ozonized liquid sprayed into the container 1 is practically in the form of an aerosol, which ensures a satisfactory distribution over the entire contents of the container and the wetting thereof throughout. In order to attain the requisite pressure it is possible for the ozone generator 21 to be followed by a suitable pressure boosting pump 24. The effective distribution of the ozone and the wetting throughout of the contents of the container may furthermore be aided by a shaking movement caused by a suitable actuation of the lifting unit 4.

As soon as the desired ozone concentrate is attained in the container, there then follows a treatment time of 30 to 40 minutes. In this time as well the contents may be shaken or agitated in order to improve the distribution and wetting of the container contents. After the elapse of the said treatment time it will be found, as a matter of experience, that the microorganisms present in the material placed in the container have been completely killed. The container contents so processed may then be dumped on a household rubbish tip without any objection. For this purpose the container contents are simply tipped out in the fashion described above.

Before tipping out the container 1 is however to be cleared of ozone in order to prevent escape of ozone into the surroundings. For this purpose the ozonized air and the ozonized water are drawn off out of the container 1 and replaced by normal air. The ozonized air can be drawn off by means of the above mentioned evacuating device in the form of the evacuating pump 11 with the container shut off and be rendered safe or inactive by use of the de-ozonizing catalyst 16 so that letting off into the surroundings is possible through the outlet port 12. After evacuation it is possible for the container 1 to be flushed with air. For this purpose it is possible to provide a flushing valve 25 which is to be able to be manually actuated. The de-ozonizing catalyst 16 returns the oxygen fraction of the ozonized air to the lower valence so that the material discharged into the surroundings consists of normal air.

The ozonized water is drawn off by means of a suction pump 26, which on the inlet side is connected with a de-ozonizing catalyst 28 for liquids, which is connected with a following outlet port 29. The suction line extends from the lower point of the container bottom, which is in the form of a sump, so that the ozonized water automatically flows to the suction line 27. The drawing off of the ozonized water and ozonized air may take place simultaneously or in sequence. Furthermore the flusing of the container may take place simultaneously with drawing off or afterwards. The evacuation line 10 may have a bleed line 10*a* branched from the port opening into its upper container part, such bleed line having means for turning it on and off and leading to the lower part of the container. The suction line 27 is, like the supply line 20, designed in the form Of a movable hose duct so that the suction pump 26 and the units following the same may be permanently installed on the chassis 2. It would however be possible to arrange them on the container 1 so that it would be possible to operate with fixed piping.

I claim:

1. A method for the disposal of material containing infective microorganisms, for example, bacteria, fungi and viruses, as well as for the disposal of waste from medical facilities, said method comprising the steps of:

introducing a substrate into a container capable of being charged with ozone;

comminuting the substrate upon introducing the substrate into said container;

charging said container with ozone;

exposing the substrate in said container, while moving the substrate relative to said container, to the action of the ozone, if necessary, via an uninterupted stream of ozone, until the infective microorganisms are killed;

discharging the ozone from said container;

converting the ozone to a lower valence level; and, evacuating said container.

2. The method as claimed in claim 1, wherein the substrate in exposed in said container to the action of ozonized air.

3. The method as claimed in claim 1, wherein the substrate in exposed in said container to the action of ozonized water.

4. The method as claimed in claim 3, further comprising the step of spraying the ozonized water into said container.

5. The method according to claim 1, further comprising the step of at least partially evacuating said container prior to said container being charged with ozone.

6. The method according to claim 1, wherein said container is at least partially evacuated upon carrying out said discharging step.

7. The method according to claim 1, wherein said exposing step is carried out for 30 to 40 minutes.

8. The method according to claim 1, wherein said charging step is carried out by charging said container with an ozone concentration corresponding to 30–40% of the total capacity of said container.

* * * * *